United States Patent [19]
de Garavilla et al.

[11] Patent Number: 5,834,025
[45] Date of Patent: Nov. 10, 1998

[54] REDUCTION OF INTRAVENOUSLY ADMINISTERED NANOPARTICULATE-FORMULATION-INDUCED ADVERSE PHYSIOLOGICAL REACTIONS

[75] Inventors: Lawrence de Garavilla, Downingtown; Elaine M. Liversidge; Gary G. Liversidge, both of West Chester, all of Pa.

[73] Assignee: Nanosystems L.L.C., King of Prussia, Pa.

[21] Appl. No.: 696,754

[22] Filed: Aug. 14, 1996

Related U.S. Application Data

[60] Provisional application No. 60/004,488 Sep. 29, 1995.
[51] Int. Cl.$^6$ ............... A61K 9/50; B32B 5/16; B01J 13/02
[52] U.S. Cl. .................. 424/501; 424/502; 428/402.21; 264/4.3
[58] Field of Search ................................ 424/501, 502; 428/402.21; 264/4.3

[56] References Cited

U.S. PATENT DOCUMENTS 5,565,188  10/1996  Wong et al. ............................ 424/499

*Primary Examiner*—Carlos Azpuru
*Attorney, Agent, or Firm*—Foley & Lardner

[57] ABSTRACT

Disclosed are methods of intravenous administration of nanoparticulate drug formulations to a mammal to avoid adverse hemodynamic effects: by reducing the rate and concentration of the nanoparticles in the formulations; or by pre-treating the subject with histamine; or by pretreating the subject with a desensitizing amount of the nanoparticulate drug formulations.

20 Claims, No Drawings

REDUCTION OF INTRAVENOUSLY ADMINISTERED NANOPARTICULATE-FORMULATION-INDUCED ADVERSE PHYSIOLOGICAL REACTIONS

BACKGROUND OF THE INVENTION

This application claims the benefit under 35 USC 119(e) of Provisional Application Number 60/004,488 filed Sep. 29, 1995.

Field of the Invention

The present invention is directed to nanoparticulate, liposome, emulsion and polymeric colloidal drug formulations for intravenous administration, the delivery of which to a mammal, reduces/eliminates the adverse physiological effects. More particularly, the invention relates to a method of intravenous nanoparticulate, liposome, emulsion and polymeric colloidal drug formulations to a mammal, wherein the rate of infusion and concentration of the drug is controlled.

Reported Developments

Nanoparticles are well know in the prior art, having been described, for example, in U.S. Pat. No. 5,145,684. These particles consist of a crystalline drug substance having a surface modifier adsorbed on the surface of the particles such that the average particle size is less than about 400 mm. Low solubility of solid drugs prompted the pharmaceutical industry to create nanoparticles of such drugs which then can be administered systematically to provide bioavailability. Drug substances disclosed which can be made into nanoparticles include a variety of known classes of drugs.

In order to provide nanometer-size particles, the drug substance is comminuted in the presence of a surface active agent or, alternatively, the surface active agent is allowed to be adsorbed to the nanoparticulate drug substance after the process of comminution. The surface active agent prevents flocculation or congregation of the nanoparticles. The achievements of nanoparticulate technology in the pharmaceutical industry affords the opportunity to prepare parenteral formulations of water-insoluble or poorly water-soluble drugs. These formulations by their nature are suspensions rather than solutions since the particles are dispersed/suspended in a pharmaceutically acceptable vehicle. Liposomes, emulsions and colloids when used as carriers for an active drug are also suspensions rather than solutions.

We have observed that intravascular adminstration of a suspensions to dogs causes significant cardiovascular dysfunction, such as reduction in arterial blood pressure and cardiac function, including heart rate cardiac output and ventricular contractility.

Other investigators have reported similar findings, for example: Slack et al., Acute Hemadynamic Effects and Blood Pool Kinetics of Polystyrene Microspheres Following Intravenous Administration, J. Pharm. Sci., 660, 1981; Faithfull et al., Cardiorespiratory Consequences of Flurocarbon Reactions in Dogs, Bio. Art. Organs, 1, 1988; and Lorenz et al., Histamine Release in Dogs by Cremophore EL and its Derivatives, Agents and Actions, 63, 1977.

It has now been discovered that hemodynamic effects of suspensions can be eliminated or at least substantially reduced by controlling the rate of infusion and/or the concentration of the active drug in the suspensions.

The present invention will be described particularly in reference to nanoparticulate crystalline drug formulations, however, the invention encompasses the use of other carriers for active drugs that do not form a solution but rather a suspension or dispersion having nanoparticulates in the range of less than 1000 nm.

SUMMARY OF THE INVENTION

This invention provides a method of administering a nanoparticulate composition to a mammal such as a dog or other sensitive species without eliciting adverse hemodynamic effects comprising:

intravenously administering to said dog an effective amount of a nanoparticulate drug composition at an infusion rate not exceeding 10 mg/min comprising particles consisting essentially of from about 0.1 to about 99.9% by weight of a crystalline organic drug substance having a solubility in water of less than 10 mg/ml, said drug substance having a surface modifier adsorbed on the surface thereof in an amount of 0.1–99.9% by weight and sufficient to maintain an effective average particle size of from about 50 to about 1000 nm, and a pharmaceutically acceptable carrier therefor.

In another embodiment, the present invention provides a method of administering a nanoparticulate composition to a mammal such as a dog or other sensitive species without eliciting adverse hemodynamic effects comprising:

intravenously administering to said dog an antihistamine including H1, H2 and H3 receptor antagonists in the amount of form about 5 to about 10 mg/kg of body weight, such as diphenhydramine, cimetidine or thioperamide or a combination thereof followed by intravenously administering to said dog an effective amount of a nanoparticulate drug composition comprising particles consisting essentially of from about 0.1 to about 99.9% by weight of a crystalline drug substance having a solubility in water of less than 10 mg/ml, said drug substance having a surface modifier adsorbed on the surface thereof in an amount of 0.1–99.0% by weight and sufficient to maintain an effective average particle size of less than 1000 nm, and preferably less than about 400 nm, and a pharmaceutically acceptable carrier thereof.

In still another embodiment the present invention provides a method of administering a nanoparticulate composition to a mammal, such as a dog or other sensitive species without eliciting adverse hemodynamic effects comprising: intravenously administering to said mammal a desensitizing amount of a nanoparticulate drug composition at an infusion rate not exceeding 10 mg/min, followed by intravenous administration of an effective amount of said nanoparticulate composition comprising particles consisting essentially of from about 0.1 to about 99.9% by weight of a crystalline organic drug substance having a solubility in water of less than 10 mg/ml, said drug substance having a surface modifier adsorbed on the surface thereof in an amount sufficient to maintain an effective average particle size of from 50 to 1000 nm, and a pharamceutically acceptable carrier therefor.

In a liposome- or colloidal-drug delivery system, the bioactive drug is entrapped in the liposome or colloidal particles in an amount of from about 0.1 to about 99.9 to about 99.1 to about 0.1% by weight liposome or colloidal particles, such particles having a particle size of less than 1000 mm, and then administered to the patient to be treated.

As used herein, the term "desensitizing amount" means a dose low enough so as not to elicit a response but still acutely precondition the mammal so that a subsequent injection of a full dose will now be without effect.

Also, as used herein, mammal preferably means a dog and other sensitive species including human species.

DETAILED DESCRIPTION OF THE INVENTION

Nanoparticulate formulations cause a significant transient decrease in arterial blood pressure immediately following intravenous injection in anesthetized dogs. Extensive studies were conducted to evaluate the acute hemodynamic effects of intravenously administered nanoparticles. To eliminate effects which may be caused by an active drug, inert polystyrene nanoparticles were used in the studies. Parameters were monitored throughout the studies including mean arterial pressure, heart rate, mean pulmonary arterial pressure, left ventricular systolic pressure, temperature, blood chemistry and hematology. In order to distinguish and separate the effects arising from components of nanoparticulate formulations, the effects of intravenous injections of: inert polystyrene nanoparticles, surfactant-coated polystyrene nanoparticles and surfactant alone were used in separate groups of dogs in the studies.

STUDY DESIGN/METHODS

A. Animals

Mongrel dogs of either sex weighing between 13 and 16 kg were used in these studies. Dogs were acquired form Butler Farms (Clyde, N.Y.) and allowed at least a two week acclimation period following shipment and prior to conducting these studies.

B. Anesthesia and Surgical Preparation

Dogs were anesthetized with sodium pentobarbital (30 mg/kg, i.v.). Following surgical preparation, the dogs were placed on an infusion of sodium pentobarbital (4 mg/kg/hr) to maintain an adequate, constant level of anesthesia throughout the experimental protocol. All anesthetic injections were administered via a 20 gauge percutaneous venicatheter placed in the right cephalic vein.

Following induction of anesthesia, dogs were placed in dorsal recumbency and intubated with a 7 French endotracheal tube and allowed to breathe room air. (Core temperature, as measured using a thermistor probe inserted 6 cm into the colon, was maintained between 37.5° and 38.5° C. using a thermostatically controlled heating pad (Harvard Homeothermic Heating Blanket, Harvard Instruments, Natick, Mass.).

The right carotid artery, right femoral artery, and the right and left femoral veins were surgically isolated via percutaneous incisions and blunt dissection. A high fidelity, solid state, dual sensor pressure transducer catheter (Model SPC 784A, Millar Instruments, Houston, Tex.) was advanced retrograde from the carotid artery and placed into the left ventricular chamber of the heart The distal pressure sensor, positioned in the left ventricle, was used to measure intraventricular pressure and the proximal sensor, positioned at the root of the aorta, measured intra-aortic pressure. The pulsatile left ventricular pressure (LVP) signal was electronically differentiated (dP/dt) to acquire an estimate of cardiac contractility (LV dP/dt). Heart rate (HR) was also derived from the pulsatile LVP signal. Mean arterial blood pressure (MAP) was derived form the pulsatile signal of intraaortic pressure. Another fluid-filled catheter was placed in the right femoral artery for acquisition of arterial blood samples for blood gas measurements. Arterial blood pH, $PCO_2$ and $pO_2$ were measured on freshly drawn samples using an automated blood gas analyzer (Model ABL30, Radiometer Corp., Westlake, Ohio). Platinum pin electrodes were inserted subcutaneously to monitor lead II electrocardiogram. All particles were injected in the left cephalic vein via a 20 gauge percutaneous venicatheter.

Following surgical preparation and instrumentation, the dogs were allowed a 30 minute acclimation period prior to initiation of the test.

C. Data Acquisition and Analysis

The following variables were continuously recorded on a pc-based automated data acquisition system (Modular Instruments, Inc., Malvern, Pa.):

Mean arterial blood pressure (MAP; mmHg)

Heart rate (HR; $min^{-1}$)

Mean pulmonary arterial blood pressure (PAP; mmHg)

Left ventricular systolic blood pressure ($LVP_{sys}$; mmHg)

Maximum left ventricular dP/dt (+LV dP/dt mmHg $sec^{-1}$)

Maximum left ventricular dP/dt (−LV dP/dt mmHg $sec^{-1}$)

The following variable were mathematically derived from the above variables and cardiac output (CO; L $min^{-1}$):

Systemic arterial vascular resistance (SVR; calculated as MAP/CO; mmHg $L^-$ min)

Pulmonary vascular resistance (PVR; calculated as PAP/CO; mmHg $L^{-1}$ min)

Stroke volume (SV; calculated as CO/HR.1000; cc).

Data were down-loaded onto a PC-based statistical package CRUNCH (Crunch Software Corporation, Oakland, Calif.). An analysis of variance followed by a Dunnett's comparison was used to test the effect of dose within each group. Between group effects (WIN 8883 vs. vehicle) were analyzed using a t-test. In all cases, data are expressed as mean±s.e.

D. Drugs and Solutions

Polystyrene Particles (Surfactant Coated)

Polystyrene particles having a diameter of 200 nm were obtained form Polysciences, Inc.

1) The Vehicle (Placebo)

A 10% solution of F108 was made by weighing out 1 g of F108 in a 50 ml plastic beaker and then adding 8 ml of water (Sterile water for injection—SWFI) to the surfactant. The beaker was placed in the refrigerator until the surfactant had gone into solution. SWIF was added to bring the final volume to 10 mls which was then filtered with a 0.1 μm syringe filter before use.

2) 5% Polystyrene Particles (PSP)+5% F108

To prepare 20 mls of 5% PSP+5% F108, 10 mls of the 200 nm particles were added to 10 mls of 10% F108 in a 50 ml centrifuge tube. The tube was placed on a mutator and the suspension was allowed to mix for 1 hour. Solutions were also prepared with 100 and 50 nm particle size polystyrene particles.

3) 5% WIN 8883+5% P108

The suspension of 5% WIN 8883+5% F108 was prepared analogously to the 5% Polystyrene+5% F108 suspension shown in #2.

4) Supernatant of 5% WIN 8883

Supernatant of WIN 8883 was prepared by centrifugation of a sample of WIN 8883 at 20,000 g for 1 hour, followed by recentrifugation of the decanted supernatant 5% WIN 8883. No WIN 8883 was found in the decanted solution.

5) Supernatant of 5% Polystyrene+5% F108

The supernatant was prepared analogously to that shown in #4. No polystyrene was found in the supernatant.

The preparations of #1, #2, #3, #4 and #5 were administered to groups of dogs subcutaneously and intravenously at various dose levels described below. Baseline hemodynamics were recorded for a 10 minute period just prior to administration of the preparations. Following administration of the preparation each dog was monitored 60 minutes.

E. Results

Results of testing are shown in the following tables.

TABLE 1

Effect of the vehicle 5% F108 and a particulate-free supernatant on the hemodynamic and hematological response in dogs when infused at a rate of 5 ml/min and a dose of 0.1 ml/kg. Values listed as means ± S.E.

| Treatment | N | % Change from Baseline MAP |
| --- | --- | --- |
| #5% F108 | 4 | −1 ± 1 |
| #5 Supernatant | 3 | −1 ± 1 | wherein:
N = no. of dogs
MAP = Mean Arterial Blood Pressure

TABLE 2

Effect of uncoated and F108 (5%) coated 200 nM diameter polystyrene nanospheres, 5% suspension, infused at a rate of 1 ml/min and a dose of 0.1 ml/kg on the hemodynamic and hematological response in dogs. Values listed as means ± S.E.

| Treatment | N | % Change from Baseline MAP |
| --- | --- | --- |
| #4 Uncoated | 3 | −1 ± 1 |
| #3 Coated | 4 | −50 ± 7 | wherein:
N = no. of dogs
MAP = Mean Arterial Blood Pressure

TABLE 3

Effect of rate of infusion of 200 nM diameter polystyrene nanospheres on the hemodynamic and hematological response in dogs. Each formulation was prepared as a 1% (w:v) suspension in a solution of 5% F108 and administered intravenously at a dose of 0.1 ml/kg. Values listed as means ± S.E.

| Rate (ml/min) | N | % Change from Baseline MAP |
| --- | --- | --- |
| 5 | 3 | −39 ± 15 |
| 1 | 4 | −26 ± 5 |
| 0.5 | 3 | −5 ± 1 | wherein:
N = no. of dogs
MAP = Mean Arterial Blood Pressure

TABLE 4

Effect of rate of infusion of 200 nM polystyrene nanospheres on the hemodynamic and hematological response in dogs. Each formulation was prepared as a 5% (w:v) suspension in a solution of 5% F108 and adminstered intravenously at a dose of 0.1 ml/kg. Values listed as means ± S.E.

| Rate (ml/min) | N | % Change from Baseline MAP |
| --- | --- | --- |
| 1 | 4 | −50 ± 7 |
| 0.1 | 3 | −1 ± 1 | wherein:
N = no. of dogs
MAP = Mean Arterial Blood Pressure

TABLE 5

Effect of pretreatment with antihistamines on the hemodynamic and hematological response in dogs following ontravenous administration of a 1% (w:v) suspension of polystyrene nanospheres, 200 nM in diameter, in a 5% solution of F108 at a dose of 0.1 ml/kg and a rate of 5 ml/min. Values listed as means ± S.E.

| Antihistamine | N | % Change from Baseline MAP |
| --- | --- | --- |
| None | 3 | −39 ± 15 |
| Diphenhydramine 10 mg/kg Cirnetidine 5 mg/kg | 4 | −7 ± 1 |
| Diaphenhydramine 10/mg/kg Cimetifine 5 mg/kg | 3 | −4 ± 2 |
| Thioperamide 5 mg/kg | | | wherein:
N = no. of dogs
MAP = Mean Arterial Blood Pressure

TABLE 6

Effect of particle size on the hemodynamic and hematological response in dogs. Each formulation was prepared as a 1% (w:v) suspension in a 5% solution of F108 and administered intravenously at a dose of 0.1 ml/kg and a rate of 5 ml/min. Values listed as means ± S.E.

| Diameter (nM) | N | % Change from Baseline MAP |
| --- | --- | --- |
| 200 | 3 | −39 ± 15 |
| 100 | 4 | −26 ± 14 |
| 50 | 3 | −8 ± 5 | wherein:
N = no. of dogs
MAP = Mean Arterial Blood Pressure

The results are summarized in Table 7.

TABLE 7

| % Solids (w/v) | Infusion Rate (ml/min) | Solids Dose Rate (mg/ml/min) | Response Y or N |
| --- | --- | --- | --- |
| 5 (50 mg/ml) | 1 | 50 | Y |
| 1 (10 mg/ml) | 10 | 100 | Y |
| 1 (10 mg/ml) | 5 | 50 | Y |
| 1 (10 mg/ml) | 1 | 10 | Y |
| 5 (50 mg/ml) | 0.1 | 5 | N |
| 10 ng/ml | 0.5 | 5 | N |

The studies indicate that there is a critical set of parameters which control hemodynamic effects in dogs. To avoid overt deleterious hemodynamic effects the following parameters should be controlled:

1) The vehicle-surfactant administered alone does not initiate a hemodynamic response.

2) "uncoated" polystyrene nanoparticles administered at a dose of 0.1 ml/kg of body weight and a rate of 1 ml/min does not induce hemodynamic effect. However, "uncoated" nanoparticle drugs cannot be administered safely, since they coagulate/flocculate causing deleterious side effects. Accordingly, active drugs must be surfactant coated to circumvent coagulation/flocculation of the nanoparticles.

3) Hemodynamic effect is associated with the surfactant-particle combination. While the inventors would not want to be limited to a theory of mechanism in the practice of their invention, it appears that the particles act as carrier for the surfactant, delivering it to its site of action in the blood stream. Theoretically, the uncoated particle also accesses the site of action but cannot initiate the response in the absence of the surfactant. Conversely, in the absence of particles, the surfactant also cannot access the site of action and does not initiate the response.

4) At a concentration of 1% solids, at 0.1 ml/kg and at infusion rate of 10 ml/min hemodynamic effects occur. At 5 ml/min delivery of the hemodynamic effect was about half of that of the 10 ml/min infusion.

5) At particle size of less than about 100 nm no hemodynamic effect occurs, while hemodynamic effect increases from 100 nm to 200 nm particle size and above 200 nm particle size.

6) Pretreatment with antihistamines to avoid hemodynamic effects. Plasma histamine levels appear to be elevated during the response. Thus the ability to block the effects of histamine at its receptor site can block the response or at least mitigate it.

Based on these and other studies the present invention provides methods which can be utilized to deliver effective amounts of drugs without eliciting adverse hemodynamic effects in dogs. The drug formulations and their methods of preparations will now be described.

Drugs

The particles comprise a therapeutic or diagnostic agent. (therapeutic agents are sometimes referred to as drugs or pharmaceuticals. The diagnostic agent referred to is typically a contrast agent such as an x-ray contrast agent but can also be other diagnostic materials.) The therapeutic or diagnostic agent exists as a discrete, crystalline phase. The crystalline phase differs from a non-crystalline or amorphous phase which results from precipitation techniques, such as described in EPO 275,796.

The invention can be practiced with a wide variety of therapeutic or diagnostic agents. The therapeutic or diagnostic agent preferably is present in an essentially pure form. The therapeutic or diagnostic agent must be poorly soluble and dispersible in at least one liquid medium. By "poorly soluble" it is meant that the therapeutic or diagnostic agent has a solubility in the liquid dispersion medium of less than about 10 mg/ml, and preferably of less than about 1 mg/ml. A preferred liquid dispersion medium is water. However, the invention can be practiced with other liquid media in which a therapeutic or diagnostic agent is poorly soluble and dispersible including, for example, aqueous salt solutions, safflower oil and solvents such as ethanol, t-butanol, hexane and glycol. The pH of the aqueous dispersion media can be adjusted by techniques known in the art.

Suitable therapeutic or diagnostic agents can be selected from a variety of known classes of therapeutic or diagnostic agents including, for example, anti-inflammatory agents, anti-arrhythmic agents, antibiotics (including penicillins), anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives (hypnotics and neuroleptics), beta-adrenoceptor blocking agents, cardiac inotropic agents, contrast media, corticosteroids, diagnostic agents, diagnostic imaging agents, dopaminergics (antiparkinsonian agents), haemostatics, immunological agents, lipid regulating agents, muscle relaxants, parasympathomimetics, parathyroid calcitonin and biphosphonates, prostaglandins, radio- pharmaceuticals, sex hormones (including steroids), anti-allergic agents, stimulants and anoretics, sympathomimetics, thyroid agents, vasodilators and xanthines. A description of these classes of therapeutic agents and diagnostic agents and a listing of species within each class can be found in Martindale, *The Extra Pharmacopoeia,* Twenty-ninth Edition, The Pharmaceutical Press, London, 1989. The therapeutic or diagnostic agents are commercially available and/or can be prepared by techniques known in the art.

Preferred diagnostic agents include the x-ray imaging agent WIN-8883 (ethyl 3,5-diacetamido-2,4, 6triiodobenzoate) also known as the ethyl ester of diatrazoic acid (EEDA), WIN 67722, i.e., (6-ethoxy-6-oxohexyl-3,5-bis(acetamido)- 2,4,6-triiodobenzoate; ethyl-2-(3,5-bis (acetamido)-2,4,6-triiodobenzoyloxy)butyrate (WIN 16318); ethyl diatrizoxyacetate (WIN 12901); ethyl 2-(3, 5bis(acetamido)-2,4,6-triiodobenzoyloxy)propionate (WIN 16923); N-ethyl 2-(3,5-bis(acetamido)-2,4, 6triiodobenzoyloxy acetamide (WIN 65312); isopropyl 2(3, 5-bis(acetamido)-2,4,6-triiodobenzoyloxy) acetamide (WIN 12855); diethyl 2-(3,5-bis(acetamido)-2,4, 6triiodobenzoyloxy malonate (WIN 67721); ethyl 2-(3,5bis (acetamido)-2,4,6-triiodobenzoyloxy) phenylacetate (WIN 67585); propanedioic acid, [[3,5-bis(acetylamino)2,4,5-triodobenzoyl]oxy]-,bis(1-methyl)ester (WIN 68165); and benzoic acid, 3,5-bis(acetylamino) 2,4,6triodo-, 4-(ethyl-3-ethoxy-2-butenoate) ester (WIN 68209). Suitable diagnostic agents are also disclosed in U.S. Pat. No. 5,260,478; U.S. Pat. No. 5,264,610; U.S. Pat. No. 5,322,679 and U.S. Pat. No. 5,300,739.

Preferred contrast agents include those which are expected to disintegrate relatively rapidly under physiological conditions, thus minimizing any particle associated inflammatory response.

Surface Modifiers

Suitable surface modifiers can preferably be selected from known organic and inorganic pharmaceutical excipients. Such excipients include various polymers, low molecular weight oligomers, natural products and surfactants. Preferred surface modifiers include nonionic and ionic surfactants.

Representative examples of surface modifiers include gelatin, casein, lecithin (phosphatides), gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, e.g., macrogol ethers such as cetomacrogol 1000, polyoxyethylene castor oil derivatives, polyoxyethylene sorbitan fatty acid esters, e.g., the commercially available Tweens™, polyethylene glycols, polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxy propylcellulose, hydroxypropylmethylcellulose phthalate, noncrystalline cellulose, magnesium aluminum silicate, triethanolamine, polyvinyl alcohol, and polyvinylpyrrolidone (PVP). Most of these surface modifiers are known pharmaceutical excipients and are described in detail in the Handbook of Pharmaceutical Excipients, published jointly by the American Pharmaceutical Association and The Pharmaceutical Society of Great Britain, the Pharmaceutical Press, 1986.

Particularly preferred surface modifiers include polyvinylpyrrolidone, tyloxapol, poloxamers such as Pluronics™ F68 and F108, which are block copolymers of ethylene oxide and propylene oxide, and polyxamines such as Tetronics™ 908 (also known as Poloxamine™ 908), which is a tetrafunctional block copolymer derived from sequential addition of propylene oxide and ethylene oxide to ethylenediamine, available from BASF, dextran, lecithin, dialkylesters of sodium sulfosuccinic acid, such as Aerosol OTs™, which is a dioctyl ester of sodium sulfosuccinic acid, available from American Cyanimid, Duponols™ P, which is a sodium lauryl sulfate, available from DuPont, Tritons™ X-200, which is an alkyl aryl polyether sulfonate, available from Rohn and Haas, Tween™ 20 and Tweens™ 80, which are polyoxyethylene sorbitan fatty acid esters, available from ICI Specialty Chemicals; Carbowaxs™ 3550 and 934, which are polyethylene glycols available from Union Carbide; Crodestas™ F-110, which is a mixture of sucrose stearate and sucrose distearate, available from Croda Inc., Crodestas™ SL-40, which is available from Croda, Inc., and SA9OHCO, which is $C_{18}H_{37}CH_2(CON(CH_3)CH_2(CHOH)_4(CH_2OH)_2$. Surface modifiers which have been found to be particularly useful include Tetronics™ 908, the Tweenss™, Pluronics™ F-68 and polyvinylpyrrolidone. Other useful surface modifiers include:

decanoyl-N-methylglucamide;
n-decyl β-D-glucopyranoside;
n-decyl β-D-maltopyranoside;
n-dodecyl β-D-glucopyranoside;
n-dodecyl β-D-maltoside;
heptanoyl-N-methylglucamide;
n-heptyl-β-D-glucopyranoside;
n-heptyl β-D-thioglucoside; n-hexyl β-D-glucopyranoside;
nonanoyl-N-methylglucamide;
n-noyl β-D-glucopyranoside;
octanoyl-N-methylglucamide;
n-octyl-β-D-glucopyranoside;
octyl β-D-thioglucopyranoside; and the like.

Another useful surface modifier is tyloxapol (a nonionic liquid polymer of the alkyl aryl polyether alcohol type; also known as superinone or triton). This surface modifier is commercially available and/or can be prepared by techniques known in the art.

Another preferred surface modifier is p-isononylphenoxypoly(glycidol) also known as Olin-10G™ or Surfactant 10-G, is commercially available as 10G™ from Olin Chemicals, Stamford, Conn.

Non-Ionic Surface Modifiers

Preferred surface modifiers can be selected from known non-ionic surfactants, including the poloxamines such as Tetronic™908 (also known as Poloxanmine™908), which is a tetrafunctional block copolymer derived from sequential addition of propylene oxide and ethylene oxide to ethylenediamine, available from BASF, or Tetronic™ 1508 (T-1508), or a polymer of the alkyl aryl polyether alcohol type, such as tyloxapol.

The surface modifiers are commercially available and/or can be prepared by techniques known in the art. Two-or more surface modifiers can be used in combination.

Auxiliary Surface Modifiers

Particularly preferred auxiliary surface modifiers are those which impart resistance to particle aggregation during sterilization and include dioctylsulfosuccinate (DOSS), polyethylene glycol, glycerol, sodium dodecyl sulfate, dodecyl trimethyl ammonium bromide and a charged phospholipid such as dimyristoyl phophatidyl glycerol. The surface modifiers are commercially available and/or can be prepared by techniques known in the art. Two or more surface modifiers can be used in combination.

Block Copolymer Surface Modifiers

One preferred surface modifier is a block copolymer linked to at least one anionic group. The polymers contain at least one, and preferably two, three, four or more anionic groups per molecule.

Preferred anionic groups include sulfate, sulfonate, phosphonate, phosphate and carboxylate groups. The anionic groups are covalently attached to the nonionic block copolymer. The nonionic sulfated polymeric surfactant has a molecular weight of 1,000–50,000, preferably 2,000–40,000 and more preferably 3,000–30,000. In preferred embodiments, the polymer comprises at least about 50%, and more preferably, at least about 60% by weight of hydrophilic units, e.g., alkylene oxide units. The reason for this is that the presence of a major weight proportion of hydrophilic units confers aqueous solubility to the polymer.

A preferred class of block copolymers useful as surface modifiers herein includes sulfated block copolymers of ethylene oxide and propylene oxide. These block copolymers in an unsulfated form are commercially available as Pluronics™. Specific examples of the unsulfated block copolymers include F68, F108 and F127.

Another preferred class of block copolymers useful herein include tetrafunctional block copolymers derived from sequential addition of ethylene oxide and propylene oxide to ethylene diamine. These polymers, in an unsulfated form, are commercially available as Tetronics™.

Another preferred class of surface modifiers contain at least one polyethylene oxide (PEO) block as the hydrophilic portion of the molecule and at least one polybutylene oxide (PBO) block as the hydrophobic portion. Particularly preferred surface modifiers of this class are diblock, triblock, and higher block copolymers of ethylene oxide and butylene oxide, such as are represented, for example, by the following structural formula:

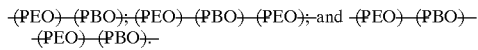

The block copolymers useful herein are known compounds and/or can be readily prepared by techniques well known in the art.

Highly preferred surface modifiers include triblock copolymers of the -(PEO-)-(PBO-)-(PEO-)-having molecular weights of 3800 and 5000 which are commercially available from Dow Chemical, Midland, Michigan, and are referred to as B20-3800 and B20-5000. These surface modifiers contain about 80% by weight PEO. In a preferred embodiment, the surface modifier is a triblock polymer having the structure:

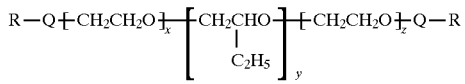

Q is an anionic group
  wherein R is H or a metal cation such as Na+, K+ and the like, x is 15-700, Y is 5-200 and z is 15-700.

Grinding

The described particles can be prepared in a method comprising the steps of dispersing a therapeutic or diagnostic agent in a liquid dispersion medium and applying mechanical means in the presence of grinding media to reduce the particle size of the therapeutic or diagnostic agent to an effective average particle size of less than about 1000 nm, and preferably of less than about 400 nm. The particles can be reduced in size in the presence of a surface modifier. Alternatively, the particles can be contacted with a surface modifier after attrition.

The therapeutic or diagnostic agent selected is obtained commercially and/or prepared by techniques known in the art in a conventional coarse form. It is preferred, but not essential, that the particle size of the coarse therapeutic or diagnostic agent selected be less than about 10 mm as determined by sieve analysis. If the coarse particle size of the therapeutic or diagnostic agent is greater than about 100 mm, then it is preferred that the particles of the therapeutic or diagnostic agent be reduced in size to less than 100 mm using a conventional milling method such as airjet or fragmentation milling.

The coarse therapeutic or diagnostic agent selected can then be added to a liquid medium in which it is essentially insoluble to form a premix. The concentration of the therapeutic or diagnostic agent in the liquid medium can vary from about 0.1–60%, and preferably is from 5–30% (w/w). It is preferred, but not essential, that the surface modifier be present in the premix. The concentration of the surface modifier can vary from about 0.1 to about 90%, and preferably is 1–75%, more preferably 20–60%, by weight based on the total combined weight of the therapeutic or diagnostic agent and surface modifier. The apparent viscosity of the premix suspension is preferably less than about 1000 centipoise.

The premix can be used directly by subjecting it to mechanical means to reduce the average particle size in the dispersion to less than 1000 nm. It is preferred that the premix be used directly when a ball mill is used for attrition. Alternatively, the therapeutic or diagnostic agent and, optionally, the surface modifier, can be dispersed in the liquid medium using suitable agitation, e.g., a roller mill or a Cowles type mixer, until a homogeneous dispersion is observed in which there are no large agglomerates-visible to the naked eye. It is preferred that the premix be subjected to such a premilling dispersion step when a recirculating media mill is used for attrition. Alternatively, the therapeutic or diagnostic agnet and, optionally, the surface modifier, can be dispersed in the iquid medium using suitable agitiation, e.g., a roller mill or a Cowles type mixer, until a homogeneous dispersion is observed in which there are no large agglomerates visible to the naked eye. It is preferred that the premix be subjected to such a premilling dispersion step when a recirculating media mill is used for attrition.

The mechanical means applied to reduce the particle size of the therapeutic or diagnostic agent conveniently can take the form of a dispersion mill. Suitable dispersion mills include a ball mill, an attritor mill, a vibratory mill, and media mills such as a sand mill and a bead mill. A media mill is preferred due to the relatively shorter milling time required to provide the intended result, desired reduction in particle size. For media milling, the apparent viscosity of the premix preferably is from about 100 to about 1000 centipoise. For ball milling, the apparent viscosity of the premix preferably is from about 1 up to about 100 centipoise. Such ranges tend to afford an optimal balance between efficient particle fragmentation and media erosion.

Preparation Conditions

The attrition time can vary widely and depends primarily upon the particular mechanical means and processing conditions selected. For ball mills, processing times of up to five days or longer may be required. On the other hand, processing times of less than 1 day (residence times of one minute up to several hours) have provided the desired results using a high shear media mill.

The particles must be reduced in size at a temperature which does not significantly degrade the therapeutic or diagnostic agent. Processing temperatures of less than about 30°–40° C. are ordinarily preferred. If desired, the processing equipment can be cooled with conventional cooling equipment. The method is conveniently carried out under conditions of ambient temperature and at processing pressures which are safe and effective for the milling process. For example, ambient processing pressures are typical of ball mills, attritor mills and vibratory mills. Control of the temperature, e.g., by jacketing or immersion of the milling chamber in ice water are contemplated. Processing pressures from about 1 psi (0.07 kg/cm2) up to about 50 psi (3.5 kg/cm2) are contemplated. Processing pressures from about 10 psi (0.7 kg/cm2) to about 20 psi 1.4 kg/cm2)

The surface modifier, if it was not present in the premix, must be added to the dispersion after attrition in an amount as described for the premix above. Thereafter, the dispersion can be mixed, e.g., by shaking vigorously. Optionally, the dispersion can be subjected to a sonication step, e.g., using an ultrasonic power supply. For example, the dispersion can be subjected to ultrasonic energy having a frequency of 20–80 kHz for a time of about 1 to 120 seconds.

After attrition is completed, the grinding media is separated from the milled particulate product (in either a dry or liquid dispersion form) using conventional separation techniques, such as by filtration, sieving through a mesh screen, and the like.

Grinding Media

The grinding media for the particle size reduction step can be selected from rigid media preferably spherical or particulate in form having an average size less than about 3 mm and, more preferably, less than about 1 mm. Such media desirably can provide the particles with shorter processing times and impart less wear to the milling equipment. The selection of material for the grinding media is not believed to be critical. We have found that zirconium oxide, such as 95% ZrO2 stabilized with magnesia, zirconium silicate, and glass grinding media provide particles having levels of contamination which are believed to be acceptable for the preparation of pharmaceutical compositions. However, other media, such as stainless steel, titania, alumina, and 95% ZrO2 stabilized with yttrium, are expected to be useful. Preferred media have a density greater than about 3 g/cm3.

Polymeric Grinding Media

The grinding media can comprise particles, preferably substantially spherical in shape, e.g., beads, consisting essentially of polymeric resin. Alternatively, the grinding media can comprise particles comprising a core having a coating of the polymeric resin adhered thereon.

In general, polymeric resins suitable for use herein are chemically and physically inert, substantially free of metals, solvent and monomers, and of sufficient hardness and friability to enable them to avoid being chipped or crushed during grinding. Suitable polymeric resins include crosslinked polystyrenes, such as polystyrene crosslinked with divinylbenzene, styrene copolymers, polycarbonates, polyacetals, such as Delrin™, vinyl chloride polymers and copolymers, polyurethanes, polyamides, poly (tetrafluoroethylenes), e.g., Teflon™, and other fluoropolymers, high density polyethylenes, polypropylenes, cellulose ethers and esters such as cellulose acetate, polyhydroxymethacrylate, polyhydroxyethyl acrylate, silicone containing polymers such as polysiloxanes and the like. The polymer can be biodegradable. Exemplary biodegradable polymers include poly(lactides), poly (glycolide) copolymers of lactides and glycolide, polyanhydrides, poly(hydroxyethyl methacylate), poly (imino carbonates), poly(N-acylhydroxyproline)esters, poly (N-palmitoyl hydroxyproline) esters, ethylene-vinyl acetate copolymers, poly(orthoesters), poly(caprolactones), and poly(phosphazenes). In the case of biodegradable polymers, contamination from the media itself advantageously can metabolize in vivo into biologically acceptable products which can be eliminated from the body.

The polymeric resin can have a density from 0.8 to 3.0 g/cm3. Higher density resins are preferred inasmuch as it is believed that these provide more efficient particle size reduction.

The media can range in size from about 0.1 to 3 mm. For fine grinding, the particles preferably are from 0.2 to 2 mm, more preferably, 0.25 to 1 mm in size.

In a particularly preferred method, a therapeutic or diagnostic agent is prepared in the form of submicron particles by grinding the agent in the presence of a grinding media having a mean particle size of less than about 75 microns.

The core material of the grinding media preferably can be selected from materials known to be useful as grinding media when fabricated as spheres or particles. Suitable core materials include zirconium oxides (such as 95% zirconium oxide stabilized with magnesia or yttrium), zirconium silicate, glass, stainless steel, titania, alumina, ferrite and the like. Preferred core materials have a density greater than about 2.5 g/cm$^3$. The selection of high density core materials is believed to facilitate efficient particle size reduction.

Useful thicknesses of the polymer coating on the core are believed to range from about 1 to about 500 microns, although other thicknesses outside this range may be useful in some applications. The thickness of the polymer coating preferably is less than the diameter of the core.

The cores can be coated with the polymeric resin by techniques known in the art. Suitable techniques include spray coating, fluidized bed coating, and melt coating. Adhesion promoting or tie layers can optionally be provided to improve the adhesion between the core material and the resin coating. The adhesion of the polymer coating to the core material can be enhanced by treating the core material to adhesion promoting procedures, such as roughening of the core surface, corona discharge treatment, and the like.

Continuous Grinding

In a preferred grinding process, the particles are made continuously rather than in a batch mode. The continuous method comprises the steps of continuously introducing the therapeutic or diagnostic agent and rigid grinding media into a milling chamber, contacting the agent with the grinding media while in the chamber to reduce the particle size of the agent, continuously removing the agent and the grinding media from the milling chamber, and thereafter separating the agent from the grinding media.

The therapeutic or diagnostic agent and the grinding media are continuously removed from the milling chamber. Thereafter, the grinding media is separated from the milled particulate agent (in either a dry or liquid dispersion form) using conventional separation techniques, in a secondary process such as by simple filtration, sieving through a mesh filter or screen, and the like. Other separation techniques such as centrifugation may also be employed.

In a preferred embodiment, the agent and grinding media are recirculated through the milling chamber. Examples of suitable means to effect such recirculation include conventional pumps such as peristaltic pumps, diaphragm pumps, piston pumps, centrifugal pumps and other positive displacement pumps which do not use sufficiently close tolerances to damage the grinding media. Peristaltic pumps are generally preferred.

Another variation of the continuous process includes the use of mixed media sizes. For example, larger media may be employed in a conventional manner where such media is restricted to the milling chamber. Smaller grinding media may be continuously recirculated through the system and permitted to pass through the agitated bed of larger grinding media. In this embodiment, the smaller media is preferably between about 1 and 300 mm in mean particle size and the larger grinding media is between about 300 and 1000 mm in mean particle size.

Precipitation Method

Another method of forming the desired nanoparticle dispersion is by microprecipitation. This is a method of preparing stable dispersions of therapeutic and diagnostic agents in the presence of a surface modifying and colloid stability enhancing surface active agent free of trace of any toxic solvents or solubilized heavy metal inpurities by the following procedural steps:

1. Dissolving the therapeutic or diagnostic agent in aqueous base with stirring, 2. Adding above #1 formulation with stirring to a surface active surfactant (or surface modifiers) solution to form a clear solution, and 3. Neutralizing above formulation #2 with stirring with an appropriate acid solution. The procedure can be followed by:

4. Removal of formed salt by dialysis or diafiltration and

5. Concentration of dispersion by conventional means.

This microprecipitation process produces dispersion of therapeutic or diagnostic agents with Z-average particle diameter less than 400 nm (as measured by photon correlation spectroscopy) that are stable in particle size upon keeping under room temperature or refrigerated conditions. Such dispersions also demonstrate limited particle size growth upon autoclave-decontamination conditions used for standard blood-pool pharmaceutical agents.

Step 3 can be carried out in semicontinuous, continuous batch, or continuous methods at constant flow rates of the reacting components in computercontrolled reactors or in tubular reactors where reaction pH can be kept constant using pH-stat systems. Advantages of such modifications are that they provide cheaper manufacturing procedures for large-scale production of nanoparticulate dispersion systems.

Additional surface modifier may be added to the dispersion after precipitation. Thereafter, the dispersion can be mixed, e.g., by shaking vigorously. Optionally, the dispersion can be subjected to a sonicationstep, e.g., using an ultrasonic power supply. For example, the dispersion can be subjected to ultrasonic energy having a frequency of 20–80 kHz for a time of about 1 to 120 seconds.

In a preferred embodiment, the above procedure is followed with step 4 which comprises removing the formed salts by diafiltration or dialysis. This is done in the case of dialysis by standard dialysis equipment and by diafiltration using standard diafiltration equipment known in the art. Preferably, the final step is concentration to a desired concentration of the agent dispersion. This is done either by diafiltration or evaporation using standard equipment known in this art An advantage of microprecipitation is that unlike milled dispersion, the final product is free of heavy metal contaminants arising from the milling media that must be removed due to their toxicity before product is formulated.

A further advantage of the microprecipitation method is that unlike solvent precipitation, the final product is free of any trace of trace solvents that may be toxic and must be removed by expensive treatments prior to final product formulation.

In another preferred embodiment of the microprecipitation process, a crystal growth modifier is used. A crystal growth modifier is defined as a compound that in the co-precipitation process incorporates into the crystal structure of the microprecipitated crystals of the pharmaceutical agent, thereby hindering growth or enlargement of the microcrystalline precipitate, by the so called Ostwald ripening process. A crystal growth modifier (or a CGM) is a chemical that is at least 75% identical in chemical structure to the pharmaceuticl agent. By "identical" is meant that the structures are identical atom for atom and their connectivity. Structural identity is charactarized as having 75% of the chemical structure, on a molecular weight basis, identical to the therapeutic or diagnostic agent. The remaining 25% of the structure may be absent or replaced by different chemical structure in the CGM. The crystal growth modifier is dissolved in step #1 with the therapeutic or diagnostic agent.

Particle Size

As used herein, particle size refers to a number average particle size as measured by conventional particle size measuring techniques well known to those skilled in the art, such as sedimentation field flow fractionation, photon correlation spectroscopy, or disk centrifugation. When photon correlation spectroscopy (PCS) is used as the method of particle sizing the average particle diameter is the Z-average particle diameter known to those skilled in the art. By "an effective average particle size of less than about 1000 nm" it is meant that at least 90% of the particles have a weight average particle size of less than about 1000 nm when measured by the above-noted techniques. In preferred embodiments, the effective average particle size is less than about 400 nm and more preferrably less than about 300 nm. In some embodiments, an effective average particle size of less than about 100 nm has been achieved. With reference to the effective average particle size, it is preferred that at least 95% and, more preferably, at least 99% of the particles have a particle size less than the effective average, e.g., 1000 nm. In particularly preferred embodiments essentially all of the particles have a size less than 1000 nm. In some embodiments, essentially all of the particles have a size less than 400 nm.

Ratios

The relative amount of therapeutic or diagnostic agent and surface modifier can vary widely and the optimal amount of the surface modifier can depend, for example, upon the particular therapeutic or diagnostic agent and surface modifier selected, the critical micelle concentration of the surface modifier if it forms micelles, the hydrophilic lipophilic balance (HLB) of the stabilizer, the melting point of the stabilizer, its water solubility, the surface tension of water solutions of the stabilizer, etc. The surface modifier preferably is present in an amount of about 0.1–10 mg per square meter surface area of the therapeutic or diagnostic agent. The surface modifier can be present in an amount of 0.1–90%, preferably 20–60% by weight based on the total weight of the dry particle.

Diagnosis

A method for diagnostic imaging for use in medical procedures in accordance with this invention comprises intravenously administering to the body of a test subject in need of a diagnostic image an effective contrast producing amount of the diagnostic image contrast composition. Thereafter, at least a portion of the body containing the administered contrast agent is exposed to x-rays or a magnetic field to produce an x-ray or magnetic resonance image pattern corresponding to the presence of the contrast agent. The image pattern can then be visualized.

Any x-ray visualization technique, preferably, a high contrast technique such as computed tomography, can be applied in a conventional manner. Alternatively, the image pattern can be observed directly on an x-ray sensitive phosphor screen-silver halide photographic film combination or by use of a storage phosphor screen.

Visualization with a magnetic resonance imaging system can be accomplished with commercially available magnetic imaging systems such as a General Electric 1.5 T Sigma imaging system [1H resonant frequency 63.9 megahertz (MHz)]. Commercially available magnetic resonance imaging systems are typically characterized by the magnetic field strength used, with a field strength of 2.0 Tesla as the current maximum and 0.2 Tesla as the current minimum. For a given field strength, each detected nucleus has a characteristic frequency. For example, at a field strength of 1.0 Tesla, the resonance frequency for hydrogen is 42.57 10 MHz; for phosphorus-31 it is 17.24 MHz; and for sodium23 it is 11.26 Mhz.

A contrast effective amount of the diagnostic agent containing composition is that amount necessary to provide tissue visualization with, for example, magnetic resonance imaging or x-ray imaging. Means for determining a contrast effective amount in a particular subject will depend, as is well known in the art, on the nature of the magnetically reactive material used, the mass of the subject being imaged, the sensitivity of the magnetic resonance or x-ray imaging system and the like.

After administration of the compositions, the subject is maintained for a time period sufficient for the administered compositions to be distributed throughout the subject and enter the tissues of the mammal. Typically, a sufficient time period is from about 20 minutes to about 90 minutes and, preferably from about 20 minutes to about 60 minutes.

The invention has been described with particular reference to preferred embodiments thereof, but it will be understood that variations and modifications can be effected within the spirit and scope of the invention.

What is claimed is:

1. A method of administering a nanoparticulate composition to a mammal without eliciting adverse hemodynamic effects comprising intravenously administering to said mammal an effective amount of a nanoparticulate drug composition at an infusion rate not exceeding 10 mg/min, wherein said drug composition comprises:

(a) particles consisting essentially of from about 0.1 to about 99.9% by weight of a crystalline organic drug substance having a solubility in water of less than 10 mg/ml;

(b) a surface modifier adsorbed on the surface of the drug substance in an amount of from about 0.1 to about 99.9% by weight and sufficient to maintain an effective average particle size of from about 50 nm to about 1000 nm; and (c) a pharmaceutically acceptable carrier therefor.

2. The method of claim 1 wherein the effective average particle size of said drug is from about 50 to about 400 nm.

3. The method of claim 1 wherein said drug is an organic therapeutic substance.

4. The method of claim 1 wherein said drug is a diagnostic agent.

5. A method of administering a nanoparticulate composition to a mammal without eliciting adverse hemodynamic effects comprising:

(a) intravenously administering to said mammal an antihistamine in the amount of from about 5 to about 10 mg/kg of body weight; and (b) subsequently intravenously administering to said mammal an effective amount of a nanoparticulate drug composition comprising: (1) particles consisting essentially of from about 0.1 to about 99.9% by weight of a crystalline drug substance having a solubility in water of less than 10 mg/ml; and (2) a surface modifier adsorbed on the surface of the drug substance in an amount of from about 99.9 to about 0.1% by weight and sufficient to maintain an effective average particle size of less than about 1000 nm.

6. The method of claim 5 wherein the effective average particle size of said drug is of from about 50 to about 400 nm.

7. The method of claim 5 wherein said drug is an organic therapeutic substance.

8. The method of claim 5 wherein said drug is a diagnostic agent.

9. A method of administering a nanoparticulate composition to a mammal without eliciting adverse hemodynamic effects comprising:

(a) intravenously administering to said mammal a desensitizing amount of a nanoparticulate drug composition at an infusion rate not exceeding 10 mg/min; and (b) intravenously administering an effective amount of said nanoparticulate composition comprising: (1) particles consisting essentially of from about 0.1 to about 99.9% by weight of a crystalline organic drug substance having a solubility in water of less than 10 mg/ml; (2) a surface modifier adsorbed on the surface of the drug substance in an amount sufficient to maintain an effective average particle size of from about 100 to about 1000 nm; and (3) a pharmaceutically acceptable carrier therefor.

10. The method of claim 9 wherein said drug is an organic therapeutic substance.

11. The method of claim 9 wherein said drug is a diagnostic agent.

12. The method of claim 9 wherein the effective average particle size of said drug is of from about 100 to about 400 nm.

13. A method of administering a nanoparticulate composition to a mammal without eliciting adverse hemodynamic effects comprising intravenously administering to said mammal an effective amount of a nanoparticulate drug composition at an infusion rate not exceeding 10 mg/min, wherein said drug composition comprises:

(a) particles having an effective average particle size of from about 50 to about 1000 nm and consisting essentially of from about 0.1 to about 99.9% by weight of an organic drug substance entrapped in from about 99.9 to about 0.1% by weight of liposome or a colloidal polymeric material; and (b) a pharmaceutically acceptable carrier therefor.

14. The method of claim 13 wherein the effective average particle size of said drug is of from about 50 to about 400 nm.

15. The method of claim 13 wherein said drug is an organic therapeutic substance.

16. The method of claim 13 wherein said drug is a diagnostic agent.

17. A method of administering a nanoparticulate composition to a mammal without eliciting adverse hemodynamic effects comprising:

(a) intravenously administering to said mammal an antihistamine in the amount of from about 5 to about 10 mg/kg of body weight; and (b) subsequently intravenously administering to said mammal an effective amount of a nanoparticulate drug composition comprising: (1) particles having an effective average particle size of from about 50 to bout 1000 nm and consisting essentially of from about 0.1 to about 99.9% by weight of an organic drug substance entrapped in from about 99.9 to about 0.1% by weight of liposome or a colloidal polymeric material; and (2) a pharmaceutically acceptable carrier therefor.

18. The method of claim 17 wherein the effective average particle size of said drug is of from about 50 to about 400 nm.

19. The method of claim 17 wherein said drug is an organic therapeutic substance.

20. The method of claim 17 wherein said drug is a diagnostic agent.

* * * * *